United States Patent
Jesurun et al.

(10) Patent No.: US 6,692,141 B2
(45) Date of Patent: Feb. 17, 2004

(54) DISPOSABLE STERILE COVER FOR SURGICAL LAMPS

(75) Inventors: David Jesurun, South Euclid, OH (US); James C. Hlebovy, Chardon, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 10/082,751

(22) Filed: Feb. 25, 2002

(65) Prior Publication Data

US 2003/0161158 A1 Aug. 28, 2003

(51) Int. Cl.$^7$ ............................................. F21V 21/08
(52) U.S. Cl. ........................................ 362/399; 362/804
(58) Field of Search ................... 362/804, 399, 362/147, 395

(56) References Cited

U.S. PATENT DOCUMENTS

| | | |
|---|---|---|
| 1,908,834 A | 5/1933 | Engberg et al. |
| 3,075,071 A | 1/1963 | Lauterbach |
| 3,891,842 A | 6/1975 | Strusinski |
| 4,316,237 A | 2/1982 | Yamada et al. |
| 4,559,671 A | 12/1985 | Andrews et al. |
| 4,605,124 A | 8/1986 | Sandel et al. |
| 4,621,735 A | 11/1986 | Coon et al. ............... 206/438 |
| D298,864 S | 12/1988 | Jefferson |
| 4,844,252 A * | 7/1989 | Barron et al. ............... 206/223 |
| 4,974,288 A | 12/1990 | Reasner |
| 4,976,299 A | 12/1990 | Bickelman |
| D313,670 S | 1/1991 | Barron et al. |
| 5,036,446 A | 7/1991 | Quintanilla et al. |
| 5,065,296 A | 11/1991 | Cude |
| 5,156,456 A | 10/1992 | Hoftman et al. |
| 5,188,454 A | 2/1993 | Quintanilla et al. |
| 4,844,252 A | 3/1993 | Barron et al. |
| 5,273,157 A | 12/1993 | Spina |
| 5,355,292 A | 10/1994 | Hoftman et al. |
| 5,465,461 A | 11/1995 | Sandel |
| 5,469,600 A | 11/1995 | Sandel |
| 5,497,295 A | 3/1996 | Gehly |
| 5,599,093 A | 2/1997 | Hoftman et al. |
| 5,604,955 A | 2/1997 | Horan |
| 5,637,863 A | 6/1997 | Sanborn et al. |
| 5,669,102 A | 9/1997 | Sandel |
| 5,700,085 A | 12/1997 | Calderwood |
| 5,709,465 A | 1/1998 | Lanzone |
| 5,803,905 A | 9/1998 | Allred et al. |
| 5,884,996 A | 3/1999 | Cottone et al. |
| D421,148 S | 2/2000 | Borders |
| D441,490 S | 5/2001 | Borders |
| 6,402,351 B1 * | 6/2002 | Borders et al. ............. 362/395 |
| 2003/0014834 A1 | 1/2003 | Naughton .................. 16/110.1 |

FOREIGN PATENT DOCUMENTS

FR 2796707 1/2001

* cited by examiner

*Primary Examiner*—Sandra O'Shea
*Assistant Examiner*—Guiyoung Lee
(74) *Attorney, Agent, or Firm*—Fay, Sharpe, Fagan, Minnich & McKee LLP

(57) ABSTRACT

An interface apparatus provides a sterile barrier between a sterile field and non-sterile portions of an associated surgical lighthead. The interface apparatus is a sterile disposable cover including a lower grippable portion, an intermediate cone-shaped portion, and an upper window area. The lower grippable portion is adapted to connect onto the handle portion of an associated surgical lighthead. An intermediate cone-shaped portion connects the lower grippable portion with an upper window area. The upper window area overlays control input means of the associated surgical lighthead such as, for example, light intensity controls. At least a portion of the upper window area is transparent to enable visualization of the control inputs beneath the sterile disposable cover. The interface apparatus is of a unitary or composite construction.

14 Claims, 4 Drawing Sheets

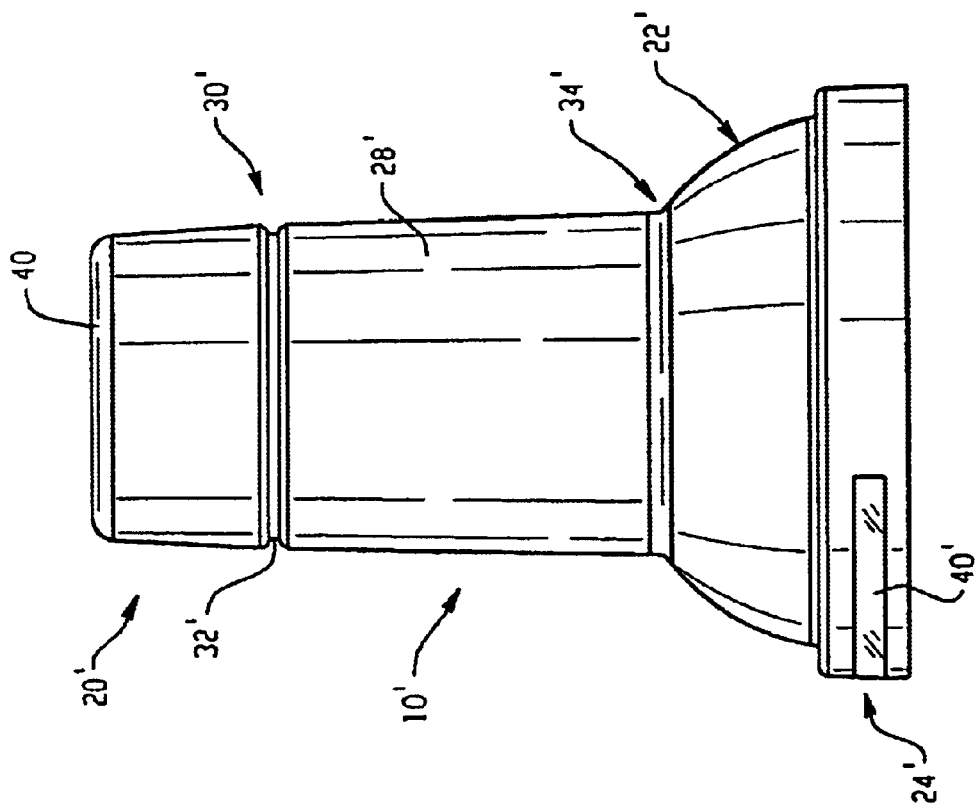
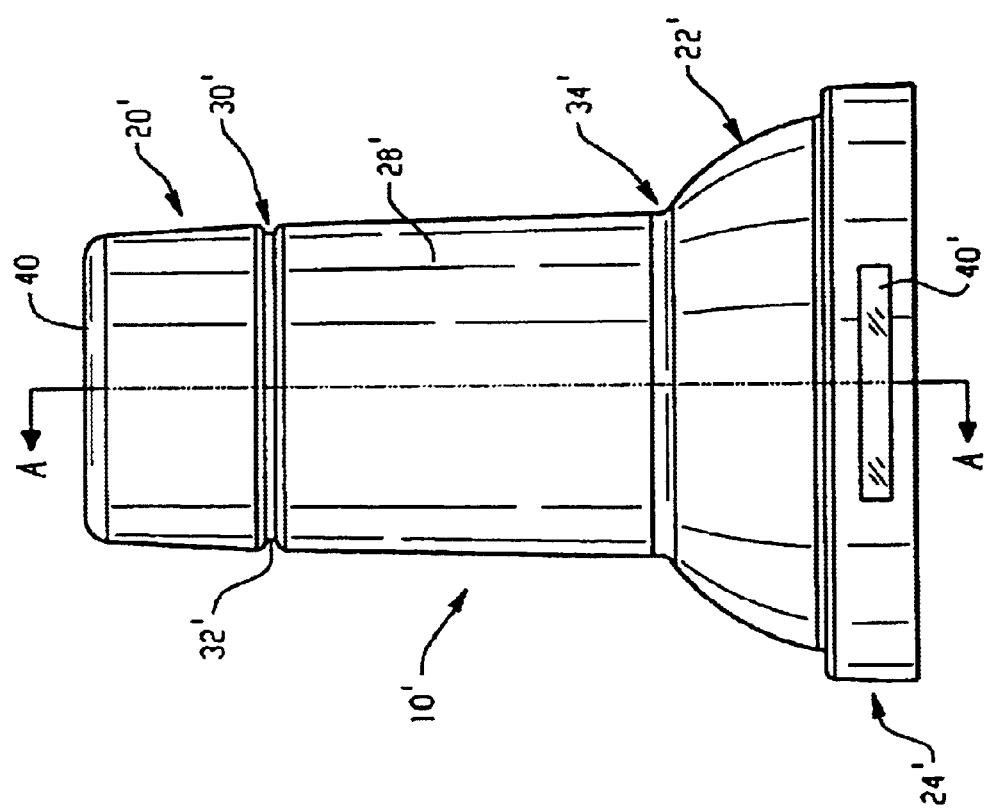

DISPOSABLE STERILE COVER FOR SURGICAL LAMPS

BACKGROUND OF THE INVENTION

The present invention relates to the surgical illumination and sterilization arts. It finds particular application in conjunction with coverings for lighthead handles and controls in an operating room setting and will be described with particular reference thereto. It is to be appreciated, however, that the invention is not limited to the aforementioned application and can be used whenever there is a need to provide an interface device between a sterile field and non-sterilized apparatus or surface.

In modern operating rooms, large overhead lightheads are used to illuminate the surgical site. The surgeon or nurse typically use manual means to position the overhead lamp, aim it at the region of interest of a patient, adjust the spot pattern of the lamp, and adjust the intensity of the lamp. To avoid unnecessary confusion and to save time, the surgeon will often manipulate the surgical lamp on his/her own. However, this requires the surfaces touched by the surgeon to be sterile in order to preserve good sterile technique.

One method of preserving good sterile technique is to sterilize portions of the lighthead with which the surgeon will interface. These portions typically include a central downwardly extending handle which the surgeon grips to move the lighthead into position, and which the surgeon can twist to adjust the beam pattern. The lighthead handles are typically removable from the surgical lighthead housing so that they can be sterilized between surgical procedures. However, sterilizing lighthead handles is time consuming and expensive.

Another method of providing a sterile interface for the surgeon is to cover portions of the lighthead handles with which the surgeon will interface with physical barriers, such as sterile plastic or rubber covers. Such covers are disposed after a single use to minimize the risk of contamination. A problem with this method is that covers capable of encasing all of the lighthead control interface components are not available, requiring a non-sterile support person to assist the surgeon. For instance, a cover might encase the handle allowing the surgeon to manipulate lighthead position and beam pattern control using the handle him/herself. However, assistance of non-sterile personnel is necessary when the light intensity is to be changed or when other controls provided on or near the lighthead are to be adjusted.

One novel approach in the surgical lighting arts proposes one or more lighting control input means such as switches on the bezel area of a surgical lighthead adjacent the handle area. This enables the surgeon to loosely grasp the lighthead handle and comfortably actuate the control buttons using the natural motion of the upwardly extended thumb. Such system is taught in co-pending provisional application serial No. 10/374,432 entitled Ergonomic Controls for a Surgical Lighting System, assigned to the assignee of the present invention and incorporated herein by reference. Although this novel solution provides a surgeon with access to lighthead control buttons, the bezel area is part of the lighthead and is therefore not sterilized with the removable handle. Simply, the controls are not in the sterile field.

Therefore, there is a need for an interface for use with surgical lightheads of the type having control input means outside of the sterile field, particularly on the bezel area adjacent the lighthead handle.

The present invention provides a new and improved method and apparatus that overcomes the above referenced problems and others. In its preferred form, the interface is a sterile disposable cover with a lower end selectively attachable to a surgical lighthead handle and with an upper end covering the lighting control switches.

SUMMARY OF THE INVENTION

The subject invention provides an interface between a sterile surgical field and control inputs on a surgical lighthead outside of the sterile field. A disposable sterile cover is provided for attachment onto the handle portion of a surgical lighthead. The cover includes a lower grippable portion with connecting means adapted to selectively attach to corresponding connecting means provided on the surgical lighthead handle. The disposable sterile cover further includes an intermediate cone-shaped portion which tapers toward an enlarged cylindrical upper window area. The lower grippable portion and intermediate cone-shaped portion are shaped in accordance with the size and shape of a standard surgical lighthead handle. A cylindrical upper window area is flexible to enable actuation of the control inputs behind the window area and includes at least one transparent area to enable viewing of control inputs on the lighthead bezel area.

A primary object of the invention is the provision of an interface between a sterile surgical field and non-sterile portions of a surgical lighthead including non-sterile lighthead control inputs.

Yet another object of the invention is the provision of an interface in the form of a disposable sterile cover selectively connectable to the handle of a standard surgical lighthead. The cover is semi-rigid so that it can be snapped into place on the lighthead handle quickly and easily. An upper portion of the sterile cover is flexible to enable operation of lighthead control inputs through the cover. In one embodiment, the cover is of a unitary construction. Alternatively, the cover is formed of two or materials forming a thin somewhat stiff lower portion attached with a thin flexible upper portion.

A still further object of the invention is the provision of a disposable sterile cover for surgical lamps including a clear lens portion to enable the cover to be used in connection with lighthead handles provided with integrated video cameras. The clear lens portion of the cover provides the optics of the integrated camera with a clear and unobstructed view path to the surgical site.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, the preferred embodiments and method of which will be described in detail in this specification and illustrated in the accompanying drawings which form a part hereof, and wherein:

FIG. 4 is a side elevational view of a disposable sterile cover formed in accordance with a second embodiment of the subject invention;

FIG. 5 is a cross-sectional view taken on line A—A of FIG. 4; and,

DETAILED DESCRIPTION OF THE INVENTION

Figure 1:
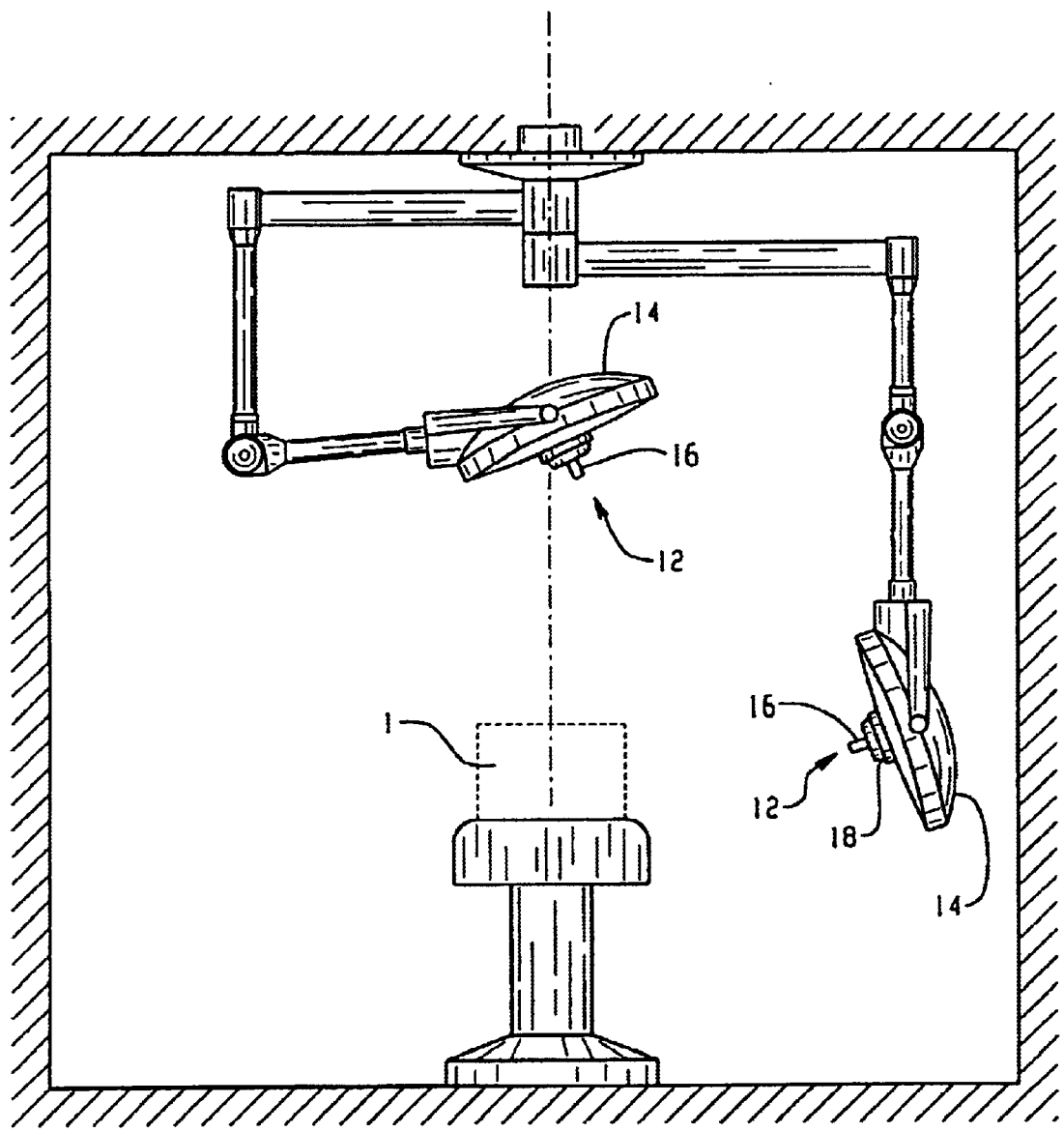
FIG. 1 is an overall view of a surgical operating room with overhead lighting devices provided with a cover in accordance with the present invention.

In a first preferred embodiment of the present invention, as can be seen in FIGS. 1–3 and 6, the sterile interface is a disposable sterile cover 10 having an overall cone shape. The subject cover provides a sterile interface between the sterile field 1 and an associated lighthead handle 12 for moving an overhead lighthead 14 into position. The subject cover further provides a sterile interface between the surgeon and lighting control inputs including a beam pattern select input 16, and intensity control inputs 18. In the illustrated embodiment of the invention 10, the pattern select control 16 is effected by rotating the lighthead handle as known in the art. The handle is also used to position the lamp manually. A plurality of lighting control input buttons 18 for controlling the intensity of the lamp are disposed on a bezel area of the lighthead directly above the handle. Functionally, the sterile cover 10 of the invention slides over and attaches onto the handle 12 covering its entirety, while simultaneously covering the plurality of lighting control buttons 18 on the bezel area of the surgical lighthead. This provides a convenient and inexpensive interface between the sterile field 1 on the outer face side of the cover 10 and non-sterile portions of the lighthead on the back side face of the cover.

Figure 3:
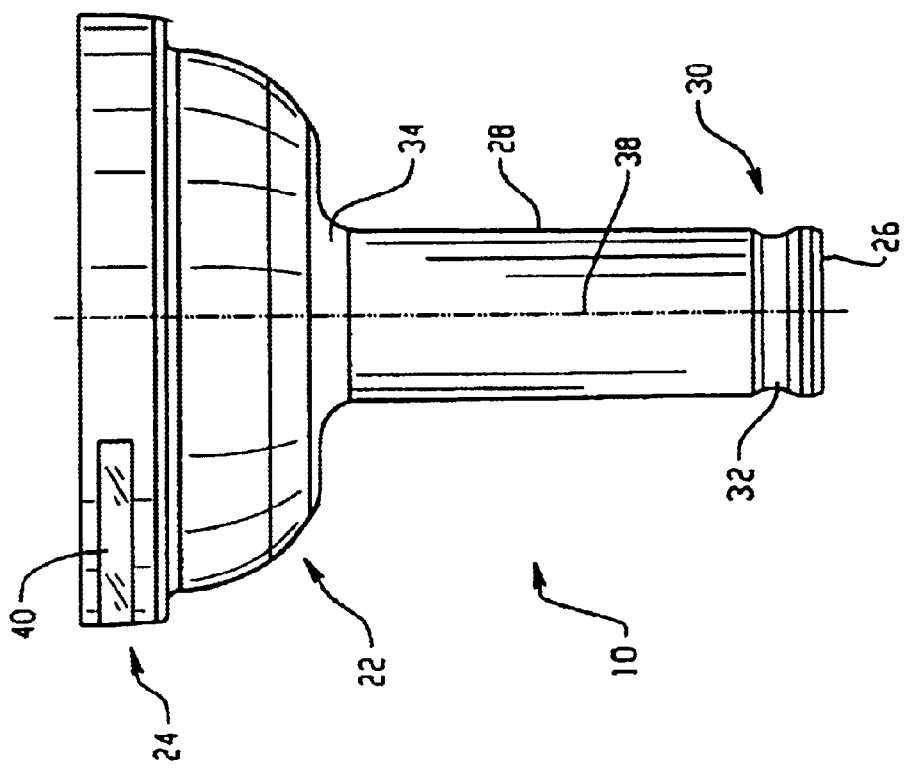
FIG. 3 is a cross-sectional view taken on line A—A of FIG. 2.
Figure 2:
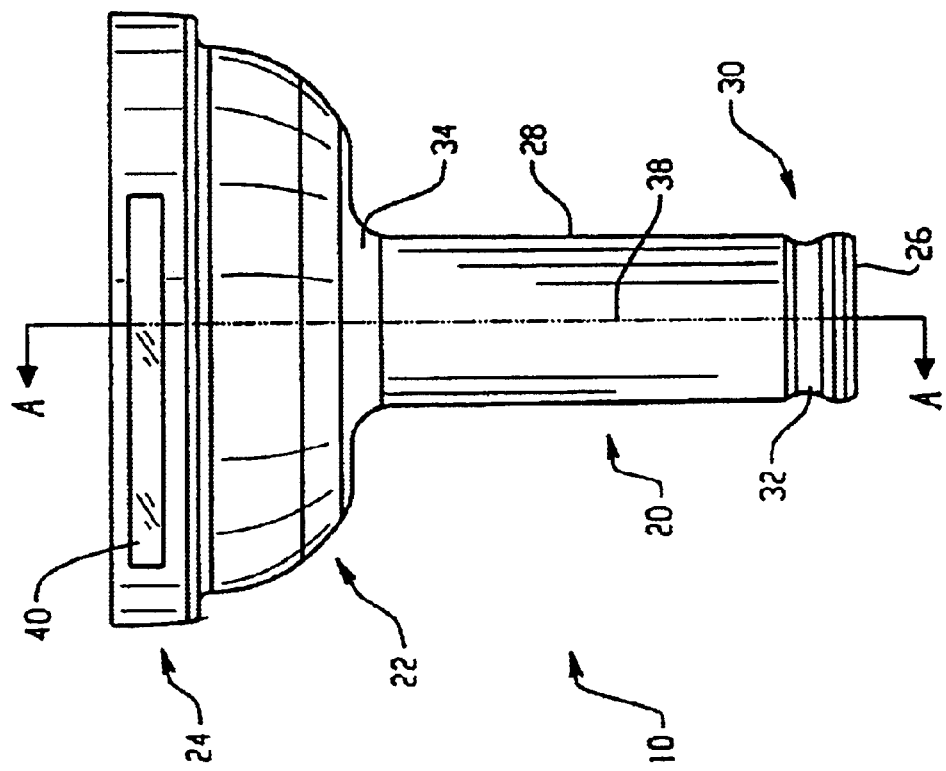
FIG. 2 is a side elevational view of a disposable sterile cover formed in accordance with a first embodiment of the subject invention.
Figure 6:
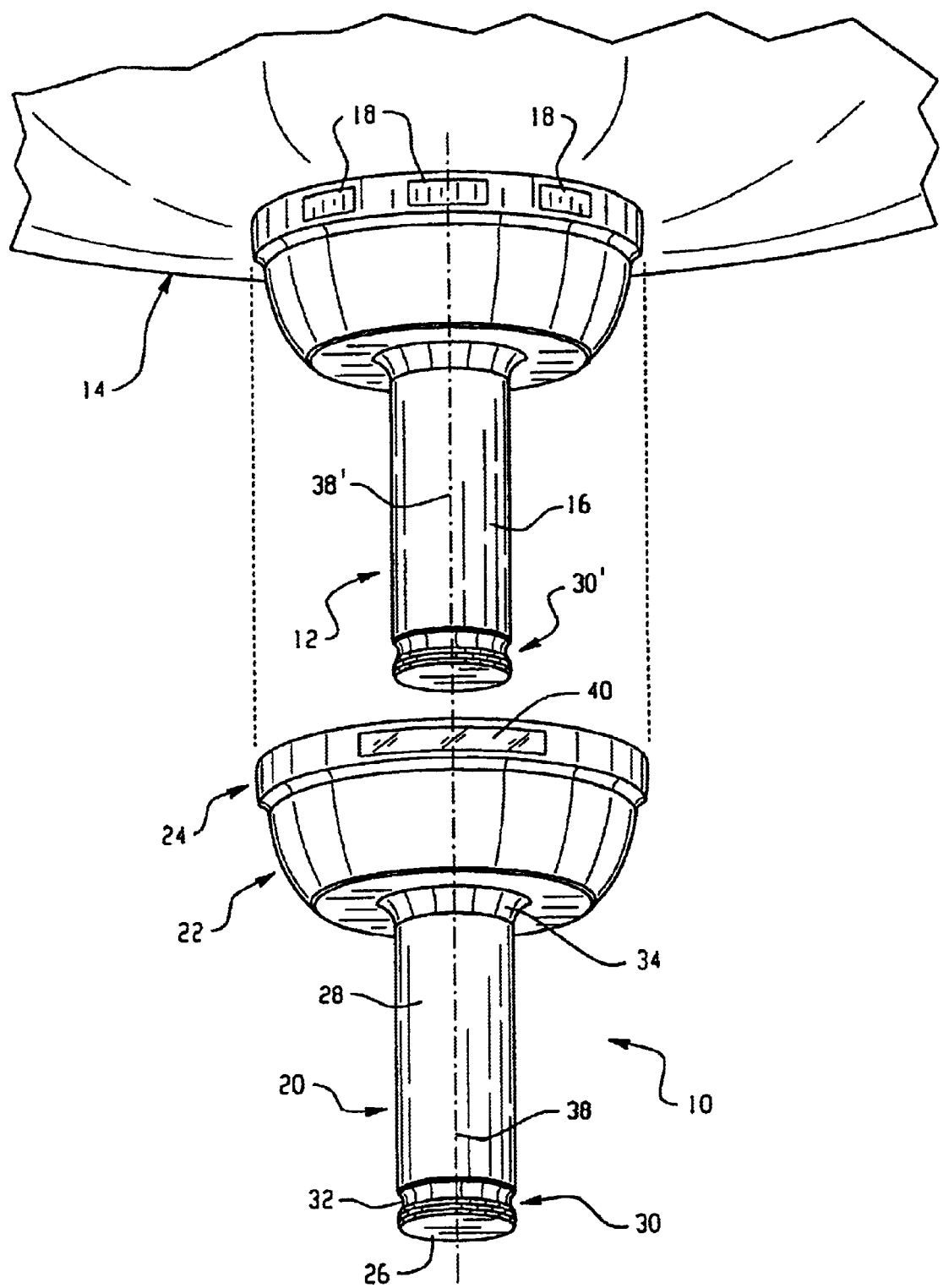
FIG. 6 is a perspective view illustrating a disposable sterile cover according to the invention being placed onto a standard surgical lighthead handle.

As shown best in FIGS. 2, 3, and 6, the sterile cover 10 of the invention is of a generally overall cup-like shape and includes a lower grippable portion 20, an intermediate cone-shaped portion 22, and an upper window area 24. The lower grippable portion 20 includes a cylindrical body portion 28 and a closed end 26 having a generally circular shape.

Connection means 30 are provided on the sterile cover 10 for attaching the cover to an associated surgical lighthead handle 12. Preferably, the connection means include one or more bands of circular grooves 32 formed circumferentially around the cylindrical body portion at one or more selected positions between the closed end 26 and a rounded region 34 opposite the closed end. In the preferred embodiment is illustrated, only a single groove is used to provide the connecting function. The connecting means 30 enables the sterile cover 10 to be easily installed onto an associated lighthead handle having a corresponding connecting means 30 as shown in FIG. 6. The rounded region provides a smooth transition between the lower grippable portion 20 and the intermediate cone-shaped portion 22. This helps guide the cover onto the handle during installation.

Preferably, the cover fits loosely around the handle and suitable contact is made at the respective connecting means areas 30, 30' so that the surgeon has the option to either rotate the cover 10 about the handle 12 such as to position a clear portion 40 over the light intensity controls 18, or firmly grasp the cover 10 and handle 12 to rotate them together such as to adjust the beam pattern. In the preferred embodiment, the mating groove 32 provides enough force to prevent the cover 10 from falling off from the handle due to gravity. Additionally, the mating groove provides enough force to prevent the surgeon from inadvertently dislodging the cover during surgery, such as by bumping it, but not so much force as to prevent the cover 10 from being removed easily after surgery.

In the embodiment shown in FIGS. 2 and 3, the cover 10 is adapted for fitting onto a standard surgical lighthead handle. Preferably, at least a portion 40 of the upper end of the cover 10 is clear so that the lighthead controls 18 are both visibly and mechanically accessible through the cover. Alternatively, the entire upper end of the cover can be formed of a clear or semi-transparent material so that the lighthead controls are visible regardless of the orientation of the cover relative to the handle.

It is to be appreciated that although grooves are preferred and only a single groove is illustrated, other intermatable shape configurations can be used on the handle and cover as well. However, in the present invention, the groove arrangement is preferred because it enables the cover 10 to rotate relative to the associated surgical lighthead handle 12 while the cover is connected to the handle. This is beneficial because the axisymmetry of the cover and handle allows the user to attach the cover without concern for relative circumferential alignment.

The intermediate cone-shaped portion 22 is essentially an extension of the lower grippable portion 20. The intermediate portion 22 is tapered as illustrated to closely surround and cover the upper portion of an associated surgical lighthead handle. Preferably, the intermediate portion has inner dimensions to provide a loose fit with minimum contact between the cover and the lighthead handle.

Preferably, the lower grippable portion 20 as well as the intermediate cone-shaped portion 22 are formed of a material to provide the cover 10 with the desired characteristics of being flexible enough to enable the connecting means 32 of the cover to snap into a corresponding connecting means 30' in the surgical lighthead handle without cracking. The material is selected to provide a disposable sterile cover 10 that supports its own weight and retains the shape illustrated while in free space. More specifically, in accordance with the present invention, the subject disposable sterile cover requires no additional external support members to maintain its shape during shipping, handling, and while being installed onto the lighthead prior to use. Although any suitable materials can be used, plastics such as thermosetting plastics and thermo formed ABS can be used as well as elastomers including synthetic rubbers, santoprene rubber, low density polyethylene, and others. Since the sterile cover 10 is disposable after each use, there is no need to form the cover from materials which can be repeatedly sterilized. In that way, cost advantages can be realized. It is to be appreciated, however, that the cover is sterilized initially, for its first use, typically by gas or radiation techniques.

Preferably, the entire cover 10 is of a unitary construction and therefore formed of a single material selected from the list above. However, the present invention contemplates forming portions of the cover from materials having different durometer values so that the upper window area 24 is softer and more flexible than the lower grippable portion. This enables the cover 10 to be rather securedly snap fitted onto the lighthead handle 12 while permitting soft action and tactile feedback through the upper area 24 while actuating the intensity control inputs 18.

With continued reference to the FIGS. 2, 3, and 6, at least a portion 40 of the upper window area 24 of the subject sterile cover 10 is formed of a transparent material to enable visualization of the lighthead controls 16, 18. Preferably, as shown in FIGS. 2 and 3, the entire ring-shaped upper window area 24 is transparent so that the control indicia are visible through the subject sterile cover 10 regardless of the orientation of the cover relative to the lighthead 14 and handle 12.

It is to be appreciated that the cover 10 is preferably symmetrical about a longitudinal axis 38 extending along each of the lower grippable portion 20, the intermediate cone-shaped portion 22, and the upper window area 24. When the cover 10 is installed onto an associated lighthead handle 12, longitudinal axis 38 of the cover is coincident and coextensive with the longitudinal axis 38' defined by the handle.

In the embodiment shown in FIGS. 4 and 5, the cover 10' is adapted for fitting onto a standard surgical lighthead handle provided with an integrated video camera. Comparison with the embodiment of FIGS. 2 and 3 shows that the lower cylindrical shaped grippable portion 20' of the cover of FIGS. 4 and 5 is somewhat wider in cross-section in order to accommodate the enlarged size of the handle with an integrated camera. In addition, the cover 10' includes a clear lens portion 40 formed on the free distal end of the cylindrical body portion 28'. This provides the optics of the camera a clear and unobstructed view path to the surgical site.

The invention has been described with reference to the preferred embodiments. Modifications and alterations will occur to others upon a reading and understanding of the preceding description. It is intended that the invention be construed as including all such modifications and alterations insofar as they come within the scope of the appended claims or the equivalents thereof.

Having thus described the preferred embodiments, the invention is now claimed to be:

1. In combination:
   a surgical lighthead;
   a lighthead control interface on the lighthead including:
      i) a handle for grasping to adjust a position of the lighthead,
      ii) first manual input means for controlling a light beam pattern emanating from the lighthead associated with the handle and,
      iii) second manual input means for controlling a light beam intensity above the handle; and,
   a cover for overlying the control interface and for providing a sterile barrier between the control interface on a first side of the cover and a sterile field on a second side of the cover opposite the first side.

2. In combination:
   a surgical lighthead;
   a lighthead control interface on the lighthead including:
      i) a handle for grasping to adjust a position of the lighthead, the handle including an annular groove therearound,
      ii) first manual input means for controlling a light beam pattern emanating from the lighthead and,
      iii) second manual input means for controlling a light beam intensity; and,
   a cover for overlying the control interface, the cover including an annular rib adapted to mate with the annular groove of the handle for positioning the cover onto the handle.

3. In combination:
   a surgical lighthead;
   a lighthead control interface on the lighthead including:
      i) a handle for grasping to adjust a position of the lighthead,
      ii) first manual input means for controlling a light beam pattern emanating from the lighthead and,
      iii) second manual input means for controlling a light beam intensity; and,
   a cover including an upper area defining a transparent portion to enable viewing the second manual input means while the cover overlays said control interface.

4. The combination as set forth in claim 2, wherein the cover is rotatable about the handle when the groove and rib are mated.

5. In combination
   a surgical lighthead;
   a handle for grasping to adjust a position of the lighthead;
   manual input means for controlling a light beam pattern emanating from the lighthead and a light beam intensity; and,
   a cover for overlying the handle and manual input means, the cover including:
      a clear lens portion on a closed distal end of the cover, the clear lens portion being adapted to provide an optical path through the cover.

6. A method of maintaining a sterile environment including:
   providing a control interface for an operating room lighthead, wherein the control interface includes light intensity controls, the light intensity controls being spaced from a handle of the lighthead;
   placing a sterile cover over the control interface, thereby preventing direct tactile access to the control interface while retaining visual access and operational functionality of the light intensity controls.

7. The method as set forth in claim 6, wherein the step of placing the sterile cover includes mating a circular connecting portion of the cover to a circular connecting portion of the control interface.

8. An interface apparatus for providing a sterile barrier between a sterile field and non-sterile handle and control input portions of an associated surgical lighthead, the interface apparatus comprising:
   a cylindrical grippable portion adapted to connect onto the handle portion of the associated surgical lighthead, the grippable portion being flexible to enable squeezing and rotating the handle portion relative to the associated surgical lighthead through the grippable portion; and,
   an upper portion carried on the cylindrical grippable portion and arranged to overlay said control input portion of the associated surgical lighthead, the upper portion being flexible to enable actuation of the control input portion of the associated surgical lighthead through the upper portion.

9. The interface apparatus according to claim 8, wherein the cylindrical grippable portion and the upper portion are of a unitary construction and formed of at least a one of an elastomer, plastic, rubber, low density polyethylene, and thermo formed APS.

10. An interface apparatus for providing a sterile barrier between a sterile field and non-sterile handle and control input portions of an associated surgical lighthead, the interface apparatus comprising:
   a cylindrical grippable portion adapted to connect onto the handle portion of the associated surgical lighthead, the grippable portion being flexible to enable squeezing and rotating the handle portion relative to the associated surgical lighthead through the grippable portion; and,
   an upper portion carried on the cylindrical grippable portion and arranged to overlay said control input portion of the associated surgical lighthead, the upper portion being flexible to enable actuation of the control input portion of the associated surgical lighthead through the upper portion, the interface apparatus being formed as a composite construction, the cylindrical grippable portion being formed of a flexible plastic and the upper portion being formed of a flexible rubber.

11. An interface apparatus for providing a sterile barrier between a sterile field and non-sterile handle and control input portions of an associated surgical lighthead, the interface apparatus comprising:

a cylindrical grippable portion adapted to receive the handle portion of the associated surgical lighthead, the grippable portion being flexible to enable squeezing and rotating the handle portion relative to the associated surgical lighthead through the grippable portion; and, an upper portion arranged to overlay said control input portions of the associated surgical lighthead, for providing a sterile barrier between a sterile field and non-sterile handle and control input portions of an associated surgical lighthead, the interface apparatus comprising:

a cylindrical grippable portion adapted to connect onto the handle portion of the associated surgical lighthead, the grippable portion being flexible to enable squeezing and rotating the handle portion relative to the associated surgical lighthead through the grippable portion; and, an upper portion carried on the cylindrical grippable portion and arranged to overlay said control input portion of the associated surgical lighthead, the upper portion being flexible to enable actuation of the control input portion of the associated surgical lighthead through the upper portion, the upper portion including a transparent area to enable the control input portions to be seen through the upper portion.

12. An interface apparatus for providing a sterile barrier between a sterile field and non-sterile handle and control input portions of an associated surgical lighthead, the interface apparatus comprising:

a cylindrical grippable portion adapted to connect onto the handle portion of the associated surgical lighthead, the grippable portion being flexible to enable squeezing and rotating the handle portion relative to the associated surgical lighthead through the grippable portion; and, an upper portion carried on the cylindrical grippable portion and arranged to overlay said control input portion of the associated surgical lighthead, the upper portion being flexible to enable actuation of the control input portion of the associated surgical lighthead through the upper portion;

a clear cover disposed on a closed distal end of the cylindrical grippable portion, the clear cover providing an unobstructed view path through the interface apparatus from the associated surgical lighthead to the sterile field.

13. In combination:

a surgical lighthead;

a handle associated with the lighthead for grasping to adjust a position of the lighthead;

a bezel area intermediate the lighthead and the handle, manual input means for controlling a light beam intensity disposed on the bezel area; and a cover for overlying the handle and bezel area, and for providing a sterile barrier between the manual input means, on a first side of the cover, and a sterile field on a second side of the cover opposite the first side.

14. A method of maintaining a sterile environment on an operating room lighthead which includes a handle and a bezel area above the handle, the handle being rotatable to adjust light beam pattern, the bezel including light intensity controls, comprising:

placing a sterile cover over the handle and the control interface, thereby preventing direct tactile access to the control interface while retaining visual access and operational functionality of the light intensity controls; and with the sterile cover in place, operating the light intensity controls.

* * * * *